(12) United States Patent
Knappe

(10) Patent No.: US 7,566,240 B2
(45) Date of Patent: Jul. 28, 2009

(54) CONSOLE WITH TWO VERTICAL SUPPORT TUBES

(75) Inventor: Stefan Knappe, Burghaun (DE)

(73) Assignee: Ondal Holding GmbH, Hunfeld (DE)

( * ) Notice: Subject to any disclaimer, the term of this patent is extended or adjusted under 35 U.S.C. 154(b) by 0 days.

(21) Appl. No.: 11/599,117

(22) Filed: Nov. 14, 2006

(65) Prior Publication Data

US 2007/0190838 A1    Aug. 16, 2007

(30) Foreign Application Priority Data

Nov. 14, 2005  (EP)  ................... 05024779

(51) Int. Cl.
*H01R 11/00* (2006.01)
(52) U.S. Cl. .................................... 439/501
(58) Field of Classification Search ................ 439/501, 439/502; 108/152, 60, 102, 50.02; 280/79.3, 280/47.35; 248/222
See application file for complete search history.

(56) References Cited

U.S. PATENT DOCUMENTS

| | | | | |
|---|---|---|---|---|
| 3,476,344 A | * | 11/1969 | Pace | 248/216.1 |
| 3,769,502 A | | 10/1973 | Schultz et al. | |
| 4,237,798 A | * | 12/1980 | Welsch et al. | 108/192 |
| 4,381,715 A | * | 5/1983 | Forman | 108/152 |
| 4,535,175 A | | 8/1985 | Squire | |
| 4,535,703 A | | 8/1985 | Henriott et al. | |
| 4,838,175 A | * | 6/1989 | Hauville | 108/25 |
| 4,998,023 A | * | 3/1991 | Kitts | 280/47.35 |
| 5,237,935 A | | 8/1993 | Newhouse et al. | |
| 5,595,428 A | | 1/1997 | Huang | |
| 5,881,500 A | * | 3/1999 | Latino et al. | 52/36.1 |
| 5,934,636 A | * | 8/1999 | Cyrell | 248/246 |
| 6,254,206 B1 | * | 7/2001 | Petrick et al. | 312/223.6 |
| 6,435,106 B2 | * | 8/2002 | Funk et al. | 108/50.02 |
| 6,467,797 B1 | * | 10/2002 | Lofy et al. | 280/647 |
| 6,675,722 B2 | | 1/2004 | Stathis et al. | |
| 6,679,722 B1 | * | 1/2004 | Pulizzi | 439/451 |
| 2006/0102054 A1 | * | 5/2006 | Warriner | 108/50.02 |

* cited by examiner

*Primary Examiner*—Alexander Gilman
(74) *Attorney, Agent, or Firm*—Seed IP Law Group PLLC

(57) ABSTRACT

With a console (1) particularly for the hospital sector, with two vertical support tubes (2), and with at least two assembly claws (3), the assembly claws (3) are mounted onto the support tubes (2) in such a way that two assembly claws (3) are next to each other on the supports tubes (2) in each case, and each of the assembly claws (3) has a plug connection (4). At least one tray (5) is provided. The tray (5) has two receptacles (6) to respectively accommodate a plug connection (4) to enable the tray (5) to be inserted onto both of the assembly claws (3). The tray (5) can be mounted on the console (1) at any height in a simple manner.

15 Claims, 3 Drawing Sheets

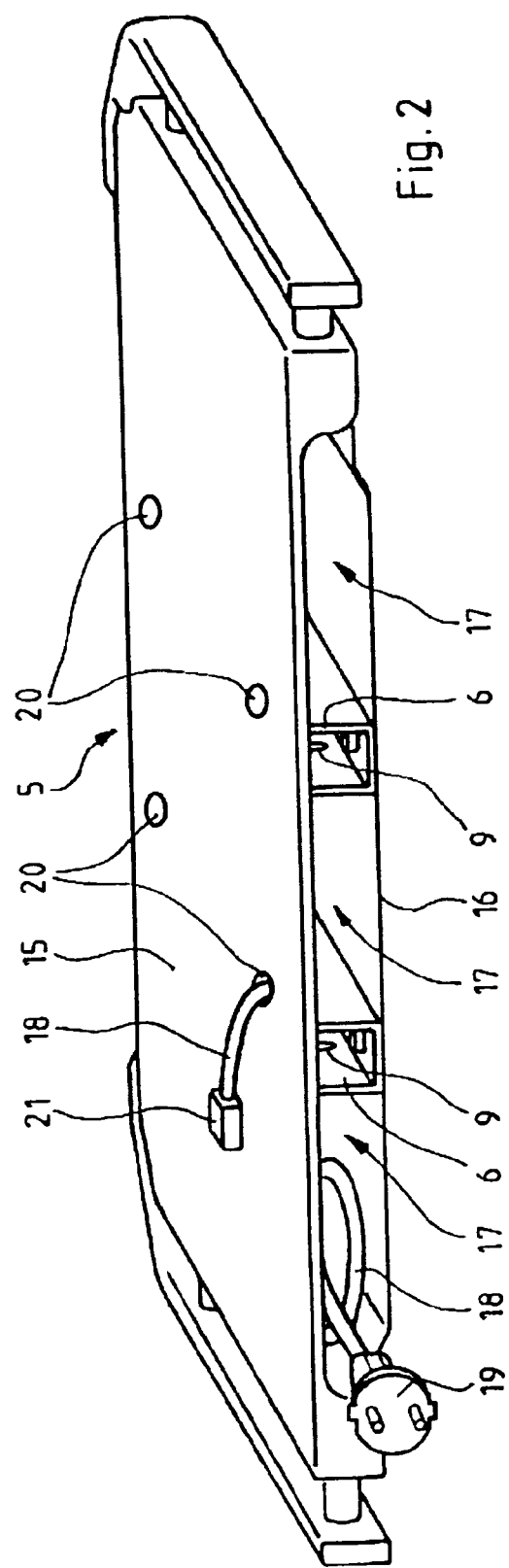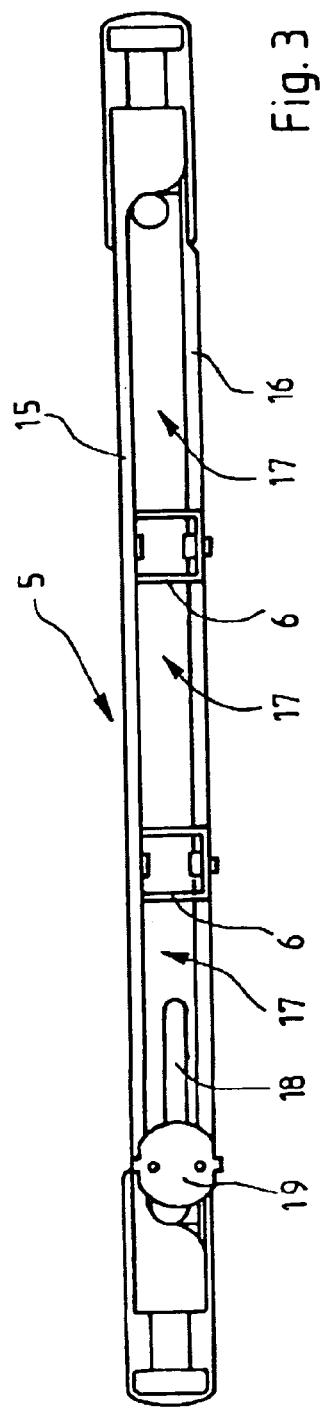

CONSOLE WITH TWO VERTICAL SUPPORT TUBES

The object of the application relates to a console, particularly for the hospital sector.

The use of consoles with trays to support medical devices is known in the hospital sector. In doing so, the devices are arranged on the trays. The electrical connection lines for the devices are routed via the trays, and the connectors for the connection lines are plugged into sockets. The trays have a simple construction and are either inserted at a certain, predetermined height using a plug system or are fixed into place at a certain height using a relatively complicated assembly device.

The object was to affix a tray of a console that can be relatively easily mounted at any height on the console.

Two vertical support tubes are provided on the console. At least two assembly claws are provided, wherein the assembly claws are mounted on the support tubes in such a manner that two assembly claws are provided next to each other on the support tubes, and wherein there is a plug connection on each of the assembly claws. Furthermore, at least one tray is provided, which has two receptacles to accommodate each of the plug connections, to enable the tray to be inserted on both of the assembly claws.

The proposed innovation has the advantage that the tray can be affixed at any desired height in a simple manner. Both of the assembly claws holding the tray can be mounted on both rods at any height that will fulfill the purposes of the medical arrangement on the tray. The plug connections are plugged into the receptacles of the tray. Thus, the assembly of the tray is carried out.

A rectangular tube is suitable as a receptacle for stabilizing the plug connections and thus the tray.

The plug connection has a ball, which is held in the plug connection, which is pre-loaded up against the plug connection using a spring, and which is provided for latching into a recess of the receptacle, then the two advantages are achieved. On one hand, the user can hear the latching and thus receives the information that the plug connections are latched into the receptacles securely. On the other hand, the ball provides resistance so that a plug connection does not come loose too easily; however, the targeted application of force will easily loosen a tray from the support tubes.

If the assembly claws consist of two claw parts, each having a gripping element, and wherein the claw parts are connected to each other using a connection element, preferably a screw, then the claw parts can then be placed on a support tube separated with the gripping element, wherein the gripping elements encompass the support tube. Once the connection element has been inserted and mounted, a plug connection that is very stably mounted on the support tube is achieved.

A securing element, preferably a screw, is provided to secure the plug connection in the receptacle, then the plug connection can be secured in its position in the receptacle in this manner.

An object can be kept within a tray if the tray has an upper wall and a lower wall and the receptacles are provided between the two walls. The areas between the walls can then be used as storage space. This type of storage space can be provided as a receptacle for electric cable, preferably along with a power plug. This ensures that cable can be safely stored with respect to its excess cable length. Obstacles due to cable or cable loops are thus prevented.

If at least one recess is provided on the upper wall, bordering a storage space, for routing electric cable having a connector socket, then cable, which is routed through a storage space (including a water supply or gas supply in addition to the electric cable), can supply a device located on the tray. Only the part of the cable extending from the recess to the device can be seen on the tray. Multiple recesses are used to route multiple cables, data lines, or the like.

If a body is provided on the console, and the body has multiple outlets, which are supplied with electrical current via an electric supply line, the electric cable that is in the storage spaces can be supplied with electricity a short distance away from a tray, without excessively long cable lines interfering. The electric supply line is preferably routed from the top down to the console. This is particularly advantageous because, in a preferred embodiment, the support tubes hang on a ceiling mount. The console could also be used in a hair salon.

The invention is described in detail below with reference to figures that show an exemplary embodiment. The following is shown:

FIG. 2 shows a perspective view of a tray according to FIG. 1;

FIG. 3 shows a side view of the tray according to FIG. 2;

Figure 1:
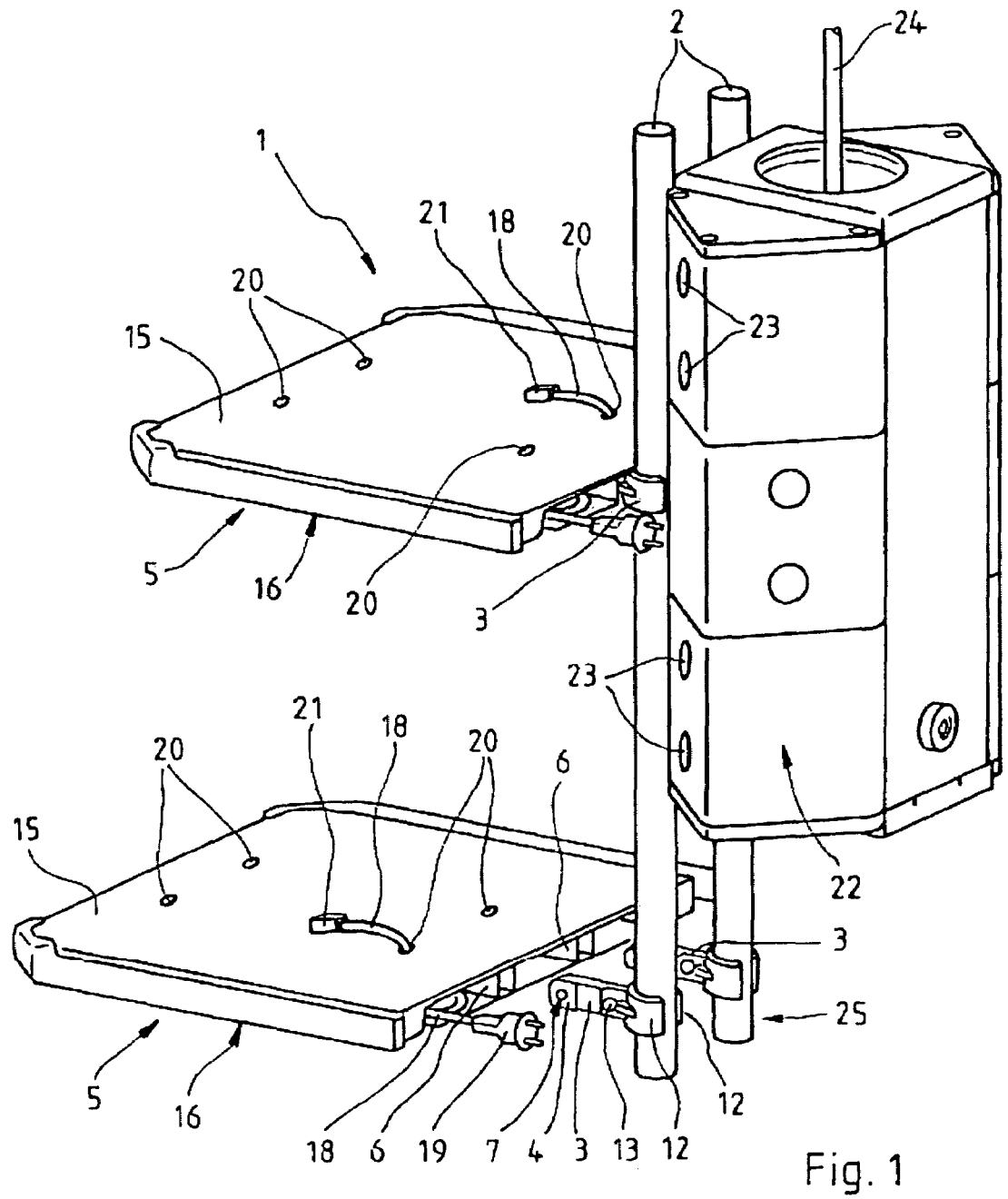
FIG. 1 shows a perspective view of the console with two vertical support tubes and two trays, each of which has storage spaces to accommodate electric cables, and which are each mounted on support tubes with two plug connections.
Figure 4:
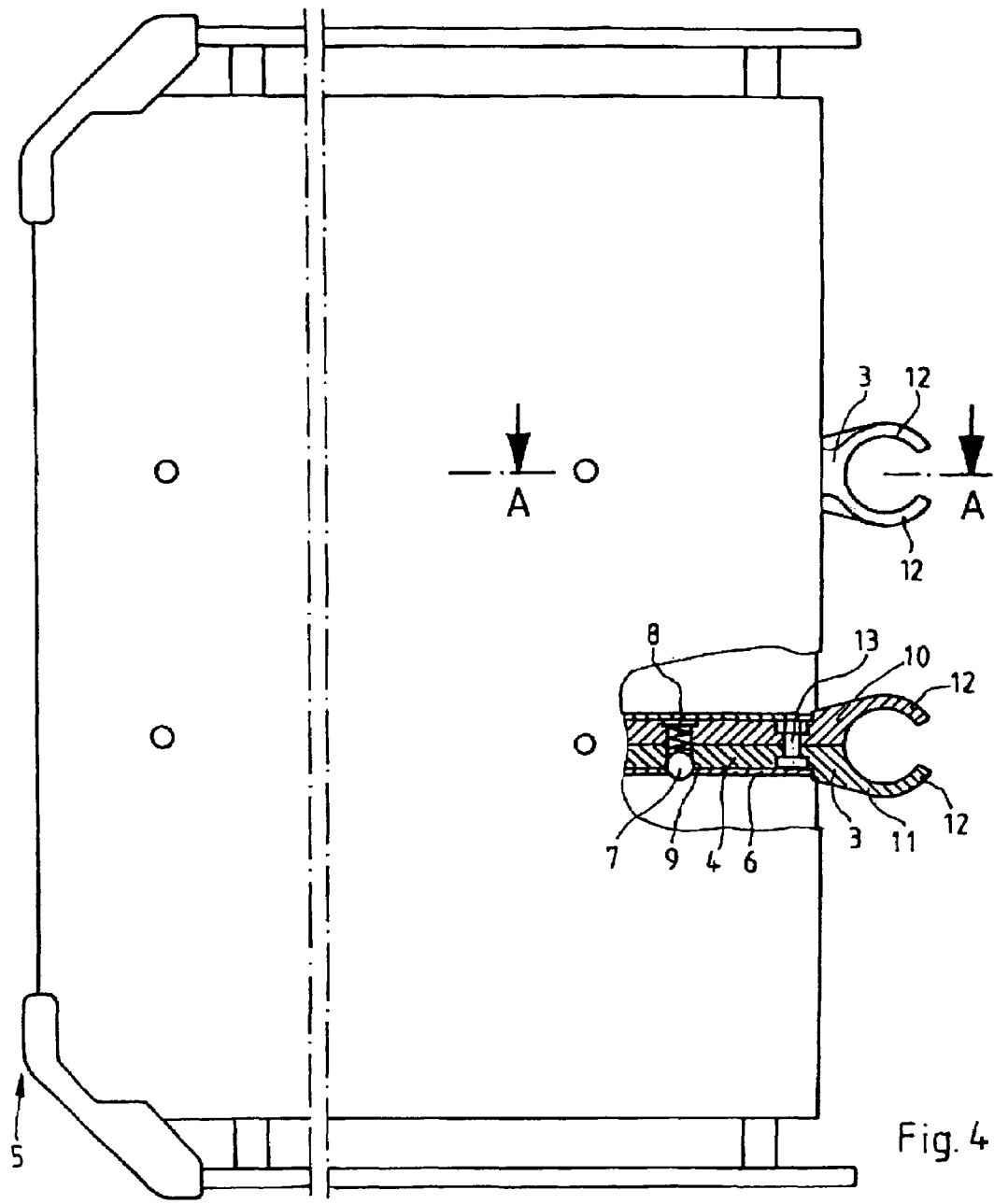
FIG. 4 shows a view from above with a partial cut-out of the tray from FIG. 2, but without the electric cable and with the plug connections inserted.
Figure 5:
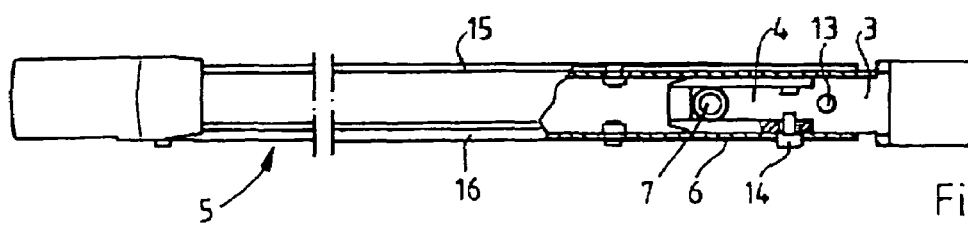
FIG. 5 shows a side view that is rotated by 90° with respect to the view in FIG. 3 with a partial cut-out of the tray from FIG. 4.

With a console 1 for the hospital sector, with two vertical support tubes 2, and with four assembly claws 3, the assembly claws 3 are mounted onto the support tubes 2 in such a way that two assembly claws 3 are provided next to each other on the supports tubes 2 in each case. Each of the assembly claws 3 has a plug connection 4. Each of the two trays have two receptacles 6 executed as a rectangular tube for the respective accommodation of a plug connection 4 to enable insertion of the tray onto the two assembly claws 3.

The plug connection 4 has a ball 7, which is held in the plug connection 4, and which is pre-loaded up against the plug connection 4 using a spring 8. The ball 7 is provided for latching into a recess 9 of the receptacle 6.

The assembly claws 3 consist of two claw parts 10,11, each of which has a gripping element 12. The claw parts 10,11 are connected to each other using a connection element 13, which is executed as a screw. A securing element 14, which is a screw, is provided for securing the plug connection 4 in the receptacle 6.

Each tray 5 has an upper wall 15 and a lower wall 16. There are two receptacles 6 and three storage spaces 17 between each of the two walls 15, 16 of a tray. The storage spaces 17 are provided for accommodating electric cables 18 along with their power plugs 19. In doing so, the power plug 19 is clamped into the storage space 17. The wall distance is measured accordingly. The upper wall 15, bordering the left and the center storage space 17, has a total of four recesses 20 for individual routing of an electric cable 18, which is subsequently provided with a connector socket 21. The connector socket 21 is used to connect a medical device. A body 22 is provided on the console 1, and the body has a multitude of outlets 23. The outlets 23 are provided with electric current via an electric supply line 24.

| | |
|---|---|
| 1 | Console |
| 2 | Support tube |
| 3 | Assembly claw |
| 4 | Plug connection |
| 5 | Tray |
| 6 | Receptacle |
| 7 | Ball |
| 8 | Spring |
| 9 | Recess |
| 10, 11 | Claw part |
| 12 | Gripping element |
| 13 | Connection element |
| 14 | Securing element |
| 15, 16 | Wall |
| 17 | Storage space |
| 18 | Electric cable |
| 19 | Power plug |
| 20 | Recess |
| 21 | Connector socket |
| 22 | Body |
| 23 | Outlet |
| 24 | Supply line |
| 25 | Assembly equipment |

The dimensions and values disclosed herein are not to be understood as being strictly limited to the exact numerical values recited. Instead, unless otherwise specified, each such dimension is intended to mean both the recited value and a functionally equivalent range surrounding that value. For example, a dimension disclosed as "40 mm" is intended to mean "about 40 mm".

All documents cited in the Detailed Description of the Invention are, in relevant part, incorporated herein by reference; the citation of any document is not to be construed as an admission that it is prior art with respect to the present invention. To the extent that any meaning or definition of a term in this written document conflicts with any meaning or definition of the term in a document incorporated by reference, the meaning or definition assigned to the term in this written document shall govern.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention.

What is claimed is:

1. A console comprising at least two substantially vertical support tubes, at least two assembly claws, and at least one tray, wherein the assembly claws are configured to be selectively mounted at a desired height on the support tubes in such a way that two assembly claws are provided next to each other on the support tubes, wherein each of the assembly claws has a plug connection which projects therefrom, the plug connections projecting in substantially parallel directions, and wherein the at least one tray has two receptacles for the respective accommodation of the plug connections, the plug connections configured to be manually slidably received in and removed from the receptacles of the tray in said substantially parallel directions to facilitate the insertion of the tray onto both of the assembly claws mounted on the support tubes.

2. The console according to claim 1, wherein a rectangular structure is provided as a receptacle.

3. The console according to claim 1, wherein the plug connection has a ball, which is held in the plug connection, which is pre-loaded up against the plug connection using a spring, and which is provided for latching into a recess of the receptacle.

4. The console according to claim 1, wherein the assembly claw consists of two claw parts, each of which has a gripping element, and wherein the claw parts are connected to each other using a connection element, preferably a screw.

5. The console according to claim 1, wherein a securing element, preferably a screw, is provided for securing the plug connection in the receptacle.

6. The console according to claim 1, wherein the tray has an upper wall and a lower wall, and wherein the receptacles are provided between the two walls.

7. The console according to claim 6, wherein at least one storage space is provided between the walls.

8. The console according to claim 7, wherein the storage space is provided for accommodating an electric cable, preferably along with a power plug.

9. The console according to claim 8, wherein, in the upper wall, bordering a storage space, at least one recess is provided for routing electric cable, which has a connector socket.

10. The console according to claim 9, wherein a body is provided on the console, and the body has a multitude of outlets, which are supplied with electric current via an electric supply line.

11. A console comprising:
    at least two substantially parallel elongated supports oriented in a substantially vertical plane;
    at least two connectors comprising gripping elements adapted to encompass the elongated supports, whereby the at least two connectors are configured to be mounted at any desired height and next to each other on the at least two supports, with one of the two connectors mounted on each support respectively, wherein the connectors project from the substantially vertical plane in substantially parallel directions when mounted on the supports; and
    at least one tray having at least two receptacles, the receptacles being configured to manually slidably receive and be removed from a respective one of the connectors mounted on the supports in said substantially parallel directions.

12. The console of claim 11, wherein the at least one tray is configured to be manually slidably received and removed from the at least two connectors via a pre-loaded amount of force.

13. The console of claim 11, wherein the at least two substantially parallel elongated supports are support tubes.

14. The console of claim 11, wherein the at least two connectors are assembly claws, each assembly claw comprising a plug connection.

15. The console of claim 14, wherein the plug connections each comprise a ball held therein, the ball being pre-loaded up against the plug connection using a spring, wherein the ball is configured to latch into a recess of the respective receptacle.

* * * * *